(12) United States Patent
    Daley

(10) Patent No.: US 8,998,916 B2
(45) Date of Patent: Apr. 7, 2015

(54) METHODS FOR DETERMINING PIN PLACEMENT DURING HIP SURGERY

(75) Inventor: Robert J. Daley, Hinsdale, IL (US)

(73) Assignee: Smith & Nephew, Inc., Memphis, TN (US)

( * ) Notice: Subject to any disclaimer, the term of this patent is extended or adjusted under 35 U.S.C. 154(b) by 527 days.

(21) Appl. No.: 13/098,548

(22) Filed: May 2, 2011

(65) Prior Publication Data

US 2011/0208201 A1    Aug. 25, 2011

Related U.S. Application Data

(62) Division of application No. 12/171,083, filed on Jul. 10, 2008.

(60) Provisional application No. 60/990,872, filed on Nov. 28, 2007, provisional application No. 60/949,135, filed on Jul. 11, 2007.

(51) Int. Cl.
    *A61B 17/58*    (2006.01)
    *A61B 17/60*    (2006.01)
    *A61F 2/00*     (2006.01)
    *A61B 17/17*    (2006.01)
    *A61B 17/56*    (2006.01)
    *A61B 19/00*    (2006.01)

(52) U.S. Cl.
    CPC ......... *A61B 17/175* (2013.01); *A61B 2017/568* (2013.01); *A61B 2019/508* (2013.01)

(58) Field of Classification Search
    USPC ..................... 606/81, 91, 89, 96, 97, 98, 104
    See application file for complete search history.

(56) References Cited

U.S. PATENT DOCUMENTS

| | | |
|---|---|---|
| 3,874,003 A | 4/1975 | Moser et al. |
| 3,882,550 A | 5/1975 | Karpf et al. |
| 3,894,297 A | 7/1975 | Mittelmeier et al. |
| 4,141,088 A | 2/1979 | Treace et al. |

(Continued)

FOREIGN PATENT DOCUMENTS

| | | |
|---|---|---|
| CN | 2638681 | 9/2004 |
| GB | 2442441 | 4/2008 |

(Continued)

OTHER PUBLICATIONS

OtisMed Website Innovation in Motion www.otismed.com, 08 pages (2008).
Brochure entitled smith&nephew Birmingham Hip Resurfacing Surgical Technique Addendum Quick Wire Femoral Alignment Jig, pp. 1-8 (2009).

(Continued)

*Primary Examiner* — Sameh Boles
(74) *Attorney, Agent, or Firm* — Ropes & Gray LLP

(57) ABSTRACT

New apparatuses and methods for their design and use are disclosed that can be used to assist a surgeon in placing a guide pin during hip surgery. Specifically, a hip surgery method is disclosed in which an image of a patient's femur can be obtained and used to design and prepare a mold that contains an aperture for guiding a drill at the desired location and angle. During surgery the mold can be quickly and accurately positioned on the exposed femur head. Then, a drill bit can be inserted through the aperture and an opening for a pin can be drilled into the femur head. The mold can have a unique contoured surface adapted to fit to the femur head in a single unique position such that the opening is made in a unique desired position. The apparatuses and methods facilitate faster, more accurate surgery and are less invasive.

20 Claims, 5 Drawing Sheets

(56) References Cited

U.S. PATENT DOCUMENTS

| | | | |
|---|---|---|---|
| 4,437,193 A | 3/1984 | Oh | |
| 4,473,068 A | 9/1984 | Oh | |
| 4,475,549 A | 10/1984 | Oh | |
| 4,623,352 A | 11/1986 | Oh | |
| 4,632,111 A | 12/1986 | Roche | |
| 4,673,409 A | 6/1987 | Van Kampen | |
| 4,676,799 A | 6/1987 | Legrand | |
| 4,718,908 A | 1/1988 | Wigginton et al. | |
| 4,795,469 A | 1/1989 | Oh | |
| 4,883,490 A | 11/1989 | Oh | |
| 4,976,740 A * | 12/1990 | Kleiner | 623/23.14 |
| 4,990,149 A | 2/1991 | Fallin | |
| 4,995,883 A | 2/1991 | Demane et al. | |
| 4,997,447 A | 3/1991 | Shelley | |
| 5,047,033 A | 9/1991 | Fallin | |
| 5,078,746 A | 1/1992 | Garner | |
| 5,080,677 A | 1/1992 | Shelley | |
| 5,098,383 A | 3/1992 | Hemmy et al. | |
| 5,108,452 A | 4/1992 | DeMane et al. | |
| 5,193,679 A | 3/1993 | White | |
| 5,217,499 A | 6/1993 | Shelley | |
| 5,226,917 A | 7/1993 | Schryver | |
| 5,310,408 A | 5/1994 | Schryver et al. | |
| 5,314,487 A | 5/1994 | Schryver et al. | |
| 5,324,291 A | 6/1994 | Ries et al. | |
| 5,350,381 A | 9/1994 | Melton | |
| 5,358,532 A | 10/1994 | Evans et al. | |
| 5,405,005 A | 4/1995 | White | |
| 5,405,392 A | 4/1995 | Deckner | |
| 5,456,717 A | 10/1995 | Zweymuller et al. | |
| 5,507,830 A | 4/1996 | DeMane et al. | |
| 5,549,702 A | 8/1996 | Ries et al. | |
| 5,569,261 A | 10/1996 | Marik et al. | |
| 5,571,105 A | 11/1996 | Gundolf | |
| 5,593,446 A | 1/1997 | Kuoni | |
| 5,676,704 A | 10/1997 | Ries et al. | |
| 5,782,928 A | 7/1998 | Ries et al. | |
| 5,824,078 A | 10/1998 | Nelson et al. | |
| 5,824,085 A | 10/1998 | Sahay et al. | |
| 5,879,405 A | 3/1999 | Ries et al. | |
| 5,931,870 A | 8/1999 | Cuckler et al. | |
| 6,059,833 A | 5/2000 | Doets | |
| 6,136,037 A | 10/2000 | Hassig et al. | |
| 6,156,069 A * | 12/2000 | Amstutz | 623/22.11 |
| 6,162,227 A | 12/2000 | Eckhardt et al. | |
| 6,259,943 B1 | 7/2001 | Cosman et al. | |
| 6,270,502 B1 | 8/2001 | Stulberg | |
| 6,325,829 B1 | 12/2001 | Schmotzer | |
| 6,344,060 B1 | 2/2002 | Schmotzer et al. | |
| 6,436,147 B1 | 8/2002 | Zweymuller | |
| 6,451,058 B2 | 9/2002 | Tuke et al. | |
| RE38,058 E | 4/2003 | Fallin | |
| 6,540,788 B1 | 4/2003 | Zweymuller | |
| 6,595,999 B2 | 7/2003 | Marchione | |
| 6,613,094 B2 | 9/2003 | Zweymuller | |
| 6,626,913 B1 | 9/2003 | McKinnon et al. | |
| 6,638,228 B1 | 10/2003 | Brock-Fisher et al. | |
| 6,652,289 B2 | 11/2003 | Bae | |
| 6,712,856 B1 | 3/2004 | Carignan et al. | |
| 6,746,452 B2 | 6/2004 | Tuke et al. | |
| 6,808,539 B2 | 10/2004 | Zweymuller | |
| 6,905,514 B2 | 6/2005 | Carignan et al. | |
| 6,916,342 B2 | 7/2005 | Frederick et al. | |
| 6,986,792 B2 | 1/2006 | McLean et al. | |
| 7,004,973 B2 | 2/2006 | Zweymuller | |
| 7,074,241 B2 | 7/2006 | McKinnon | |
| 7,160,307 B2 | 1/2007 | Harwood et al. | |
| 7,160,332 B2 | 1/2007 | Frederick et al. | |
| 7,175,668 B2 | 2/2007 | Zweymuller | |
| 7,179,297 B2 | 2/2007 | McLean | |
| 7,250,054 B2 | 7/2007 | Allen et al. | |
| 7,255,701 B2 | 8/2007 | Allen et al. | |
| 7,335,231 B2 | 2/2008 | McLean | |
| 7,374,576 B1 | 5/2008 | Ries et al. | |
| 7,455,693 B2 | 11/2008 | Zweymuller | |
| 7,494,510 B2 | 2/2009 | Zweymuller | |
| 7,497,875 B1 | 3/2009 | Zweymuller | |
| 7,534,263 B2 | 5/2009 | Burdulis, Jr. et al. | |
| 7,534,271 B2 | 5/2009 | Ries et al. | |
| 7,575,603 B2 | 8/2009 | Bergin et al. | |
| 7,591,821 B2 | 9/2009 | Kelman | |
| 7,621,915 B2 | 11/2009 | Frederick et al. | |
| 7,682,398 B2 | 3/2010 | Croxton et al. | |
| 7,749,277 B2 | 7/2010 | McLean | |
| 7,749,278 B2 | 7/2010 | Frederick et al. | |
| 7,780,667 B2 | 8/2010 | Watanabe et al. | |
| 7,828,806 B2 | 11/2010 | Graf et al. | |
| 7,862,570 B2 | 1/2011 | Russell et al. | |
| 7,863,410 B2 | 1/2011 | Smith et al. | |
| 7,879,106 B2 | 2/2011 | McMinn | |
| 7,892,290 B2 | 2/2011 | Bergin et al. | |
| 7,901,411 B2 | 3/2011 | Frederick et al. | |
| 7,981,158 B2 | 7/2011 | Fitz et al. | |
| 2003/0055502 A1 | 3/2003 | Lang et al. | |
| 2003/0216669 A1 | 11/2003 | Lang et al. | |
| 2004/0133276 A1 | 7/2004 | Lang et al. | |
| 2004/0138754 A1 | 7/2004 | Lang et al. | |
| 2004/0204644 A1 | 10/2004 | Tsougarakis et al. | |
| 2004/0236424 A1 | 11/2004 | Berez et al. | |
| 2005/0119664 A1 | 6/2005 | Carignan et al. | |
| 2005/0148843 A1 | 7/2005 | Roose | |
| 2005/0234461 A1 | 10/2005 | Burdulis, Jr. et al. | |
| 2006/0122617 A1 | 6/2006 | Lavallee et al. | |
| 2007/0198022 A1 | 8/2007 | Lang et al. | |
| 2008/0287954 A1 * | 11/2008 | Kunz et al. | 606/87 |
| 2008/0312659 A1 | 12/2008 | Metzger et al. | |
| 2009/0018546 A1 | 1/2009 | Daley | |
| 2009/0118736 A1 | 5/2009 | Kreuzer | |
| 2009/0222015 A1 | 9/2009 | Park et al. | |
| 2009/0222016 A1 | 9/2009 | Park et al. | |
| 2009/0254093 A1 * | 10/2009 | White et al. | 606/89 |
| 2010/0016986 A1 | 1/2010 | Trabish | |
| 2010/0286700 A1 | 11/2010 | Snider et al. | |
| 2011/0015637 A1 | 1/2011 | De Smedt et al. | |

FOREIGN PATENT DOCUMENTS

| | | |
|---|---|---|
| WO | WO9325157 | 12/1993 |
| WO | WO-00/59411 A1 | 10/2000 |
| WO | WO-2006079211 A1 | 8/2006 |
| WO | WO2007137327 | 12/2007 |
| WO | WO2008014618 | 2/2008 |
| WO | WO2009001109 | 12/2008 |
| WO | WO2009009660 | 1/2009 |
| WO | WO2010129870 | 11/2010 |

OTHER PUBLICATIONS

Brochure entitled smith&nephew Birmingham Hip Resurfacing System Surgical Technique, pp. 1-50 (2007).

International Search Report and Written Opinion dated Aug. 4, 2010 in related Application No. PCT/US2010/034043.

Eckhoff, et al., "Three-Dimensional Mechanics, Kinematics and Morphology of the Knee Viewed in Virtual Reality," *The Journal of Bone and Joint Surgery (American)*, 87:71-80 (2005).

Raaijmaakers, et al., "A custom-made guide-wire positioning device for Hip Surface Replacement Arthroplasty: description and first results," *BMC Musculoskeletal Disorders*, 11:161 (2010).

Radermacher, et al., "Computer Assisted Orthopaedic Surgery With Image Based Individual Templates," *Clinical Orthopaedics and Related Research*, 354:28-38 (1998).

Preliminary Amendment dated Aug. 6, 2009 in U.S. Appl. No. 12/171,083.

Office Action dated Feb. 11, 2011 in U.S. Appl. No. 12/171,083.

Response dated Apr. 28, 2011 in U.S. Appl. No. 12/171,083.

Office Action dated May 26, 2011 in U.S. Appl. No. 12/171,083.

Chao et al., "Computer-Aided Preoperative Planning in Knee Osteotomy," The Iowa Orthopaedic Journal, 15:4-18 (1995).

Office Action dated Feb. 3, 2012 in U.S. Appl. No. 12/171,083.

* cited by examiner

METHODS FOR DETERMINING PIN PLACEMENT DURING HIP SURGERY

PRIORITY CLAIM

This application is a divisional application of U.S. application Ser. No. 12/171,083, filed Jul. 10, 2008 and entitled "METHODS AND APPARATUS FOR DETERMINING PIN PLACEMENT DURING HIP SURGERY," which itself claims priority to U.S. Provisional Application Ser. No. 60/990,872, filed Nov. 28, 2007 and entitled "METHODS AND APPARATUS FOR DETERMINING PIN PLACEMENT DURING HIP SURGERY" and U.S. Provisional Application Ser. No. 60/949,135, filed Jul. 11, 2007 and entitled "METHOD AND APPARATUS FOR DETERMINING PIN PLACEMENT DURING HIP SURGERY", the entire contents of which are hereby incorporated by reference.

TECHNICAL FIELD

The present application relates generally to an apparatus and methods for hip surgery.

BACKGROUND

In the resurfacing of a femur head in a patient's hip, installation of a new surface on the femur head with resurfacing device can require that a guide for a drill be installed on a suitable axis of the head/neck of the patient's femur. The axis of the drill guide is determined prior to surgery by a surgeon through analysis of an X-ray or other image of the femur. Prior to implanting the new surface device, the femoral head is typically machined to a suitable shape having a central axis. The axis is determined by the drill guide. The success of the surgery, in important part, is determined by the placement of the drill guide. It has long been a problem in the art to accurately locate the drill guide, so that the resurfacing device itself can subsequently be accurately fitted.

SUMMARY

New apparatuses and methods for their design and use are disclosed that can be used to assist a surgeon in more rapidly and accurately placing a guide pin during hip surgery. Specifically, a hip surgery method is disclosed in which an image of a patient's femur can be obtained and used to design and prepare a mold that contains an aperture for guiding a drill at the desired location and angle. During surgery the mold can be quickly and accurately positioned on the exposed femur head. Then a drill bit can be inserted through the aperture and an opening for a pin can be drilled into the femur head. The mold can have a unique contoured surface adapted to fit to the femur head in a single unique position. The apparatuses and methods facilitate faster, more accurate surgery and are less invasive.

Additional features and advantages are described herein, and will be apparent from, the following Detailed Description and the figures.

DETAILED DESCRIPTION

A mold for a femur head is disclosed that is defined, in part, by a contoured surface adapted to contact the surface of a femur head. The mold further defines an aperture that can be used as a guide for a drill bit that can be used to drill an opening in the femur head for holding a pin, such as a guide pin, during a femur resurfacing procedure.

The mold can be made of any abrasion resistant hard material, of which many are known, that can be used to guide a drill bit during hip surgery. As can be appreciated, suitable materials will be able to withstand sterilization procedures such that they can be used in surgery and will not be toxic to the surgeon or patient. Suitable materials include metals and plastics, particularly thermosetting plastics.

Figure 1:
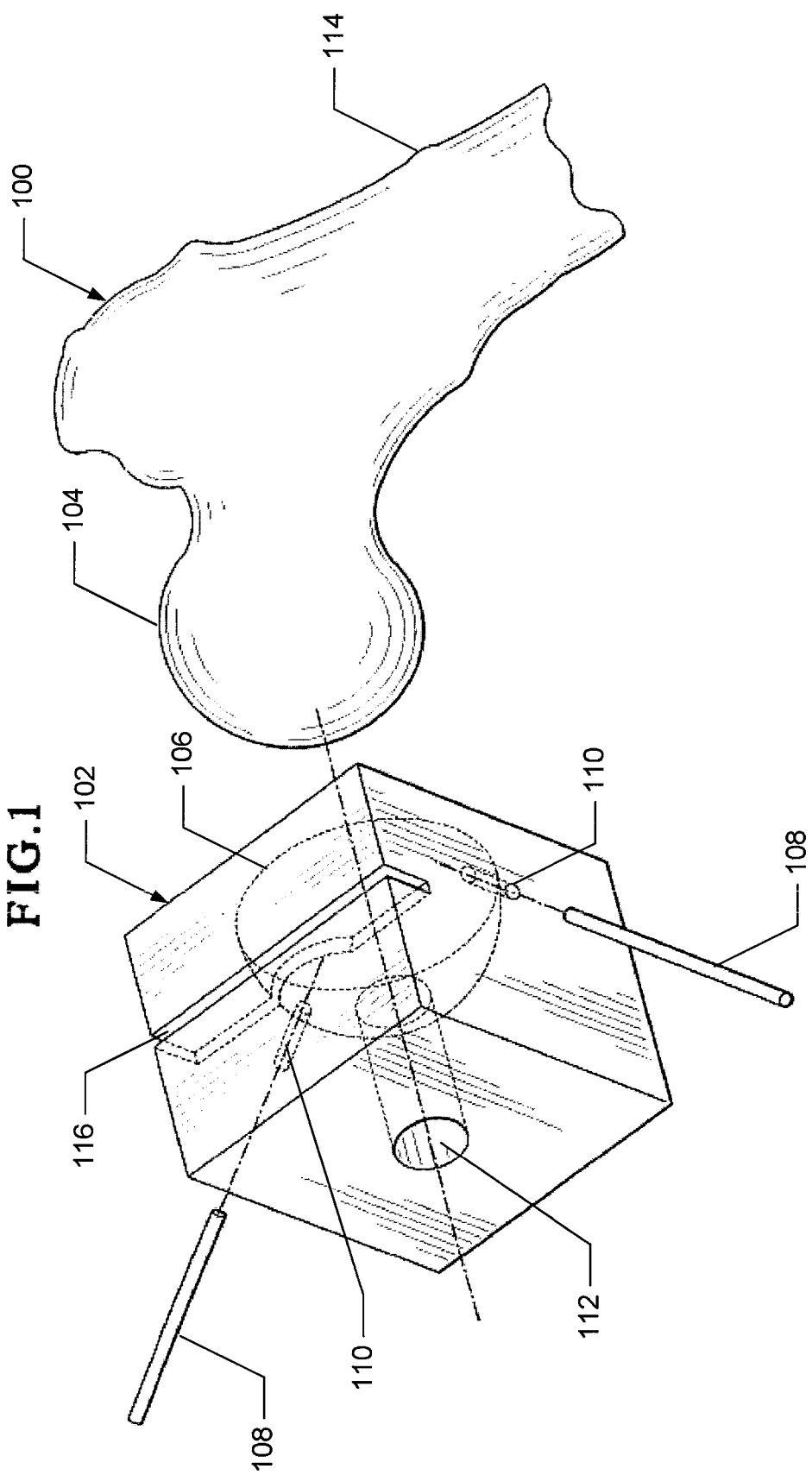
FIG. 1 is a perspective view of a femoral head positioned for insertion in to an example block-shaped alignment mold.
Figure 2:
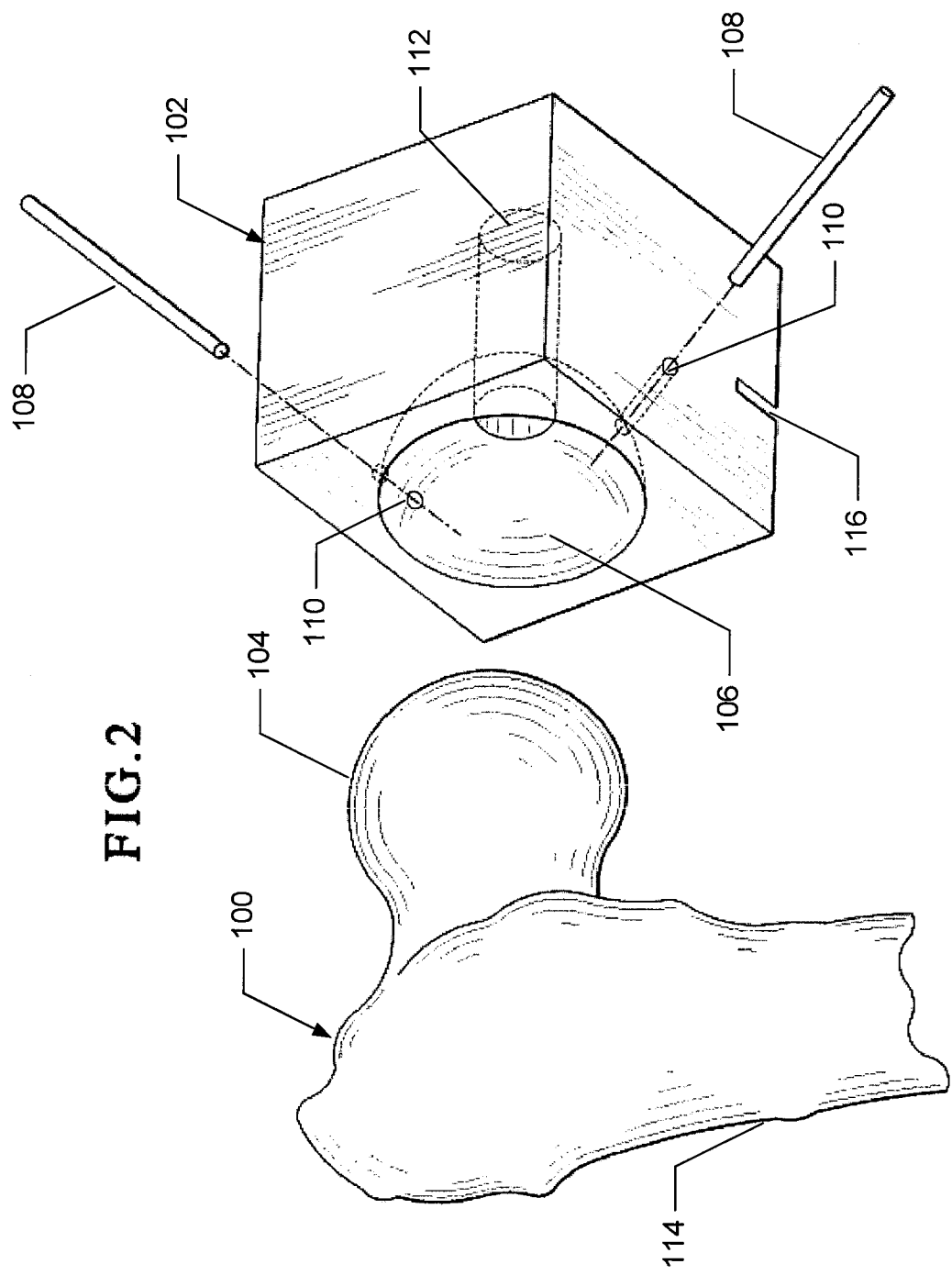
FIG. 2 is another perspective view of the femoral head positioned for insertion in to the example block-shaped alignment mold.

Turning to FIG. 1 and FIG. 2, a patient's femur 100 can be measured before a surgery using a scanner such as an X-ray machine, a magnetic resonance imaging (MRI) device, and/or a computed tomography (CT) scanner and the like. A surgeon then can use the image(s) to determine the desired location and angle for insertion of a pin into the femur head. Data from the scanner and the surgeon's selections can then be used to create a mold 102 that fits the femur head 104. For example, MRI data may be transmitted to a company with software that evaluates critical angles and geometry associated with the femur and uses a computer aided design/computer aided manufacturing (CAD/CAM) system to produce the mold 102. In a preferred method, the mold 102 is designed so that it has a unique contoured surface 106 that is adapted to mate with a unique portion of the surface of the femur head 104. Such a design facilitates positioning of the mold 102 on the femur head 104 such that an aperture 112 can guide a drill bit into an optimal location for placement of the pin during surgery. In such a position, the aperture 112 defines an axis in the femur head 104, which may substantially correspond with an axis in the femur head 104 that is in line with a femur neck 114. The mold 102 can then be shipped to the hospital and prepared for surgery.

In some surgical procedures it can be desirable to also place a cut into the femur head 104 such as in a procedure known as an osteotomy. To facilitate making a suitable cut, a slot or guide 116 can be included in the mold 102. The slot 116 can be included in the mold 102 such that it defines an angle, a position and/or a depth for such a cut into the femur head 104 when the mold 102 is positioned on the femur head 104.

In certain embodiments the mold 102 can be designed such that it contains one or more pin placement apertures 110 for anchor pins 108. The mold 102 can then be placed on the femur 100, and the anchor pins 108 can be inserted through the pin placement apertures 110 into the femur head 104 to securely affix the mold 102 to the femur head 104 while the mold 102 is used during surgery.

Figure 3:
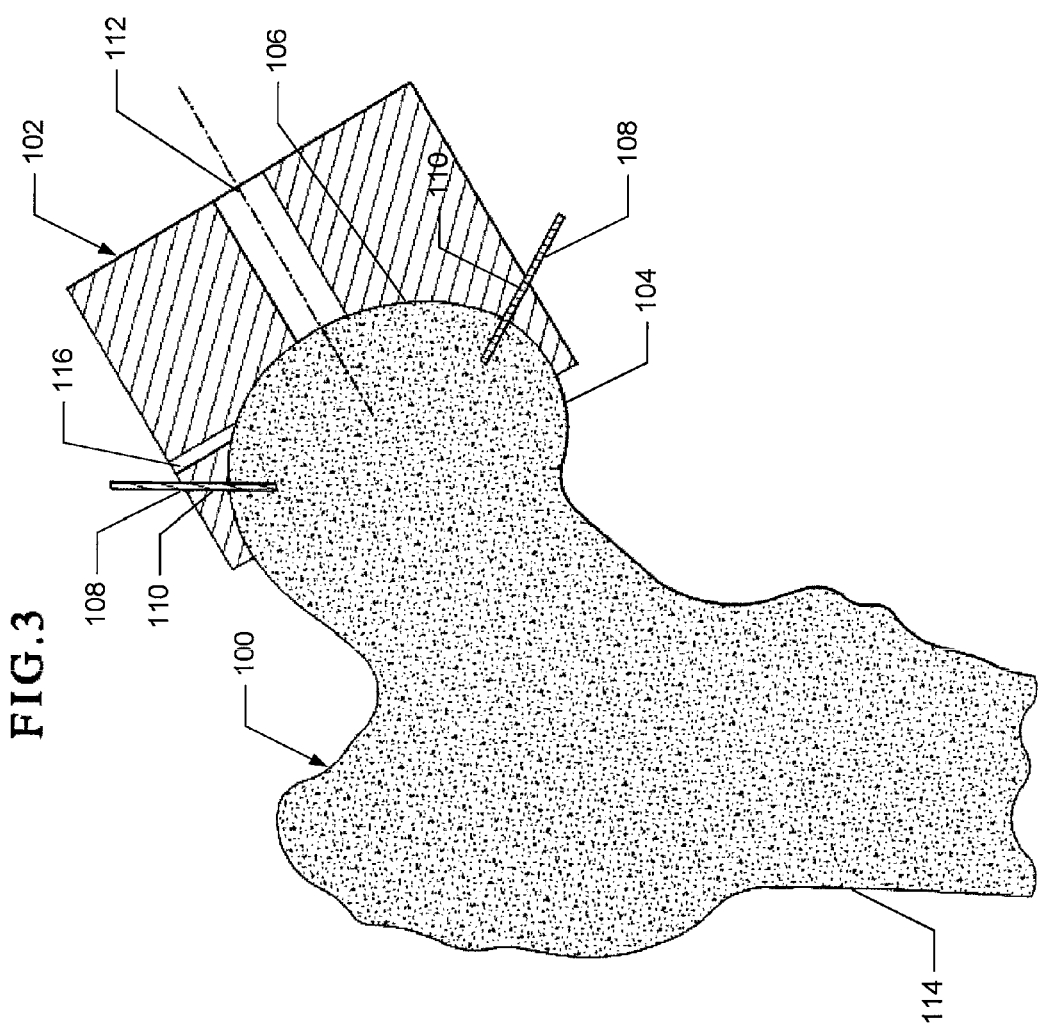
FIG. 3 is a cross-sectional view of the femoral head positioned for insertion in to the example block-shaped alignment mold.

FIG. 3 illustrates a mold 102 in contact with a femur head 104 and further illustrates a uniquely contoured contact surface 106 of the mold 102 in contact with a unique contour of the femur head 104. As can be seen in the embodiment of FIG. 3, when affixed to femur head 104, the aperture 112 of the mold 102 can be substantially aligned with an axis of the femur head 104 in line with the femur neck 114. FIG. 3 further illustrates the pins 108 extending through the pin placement apertures 110 and into the femur head 104 to securely hold the mold 102 to the femur head 104.

Figure 4:
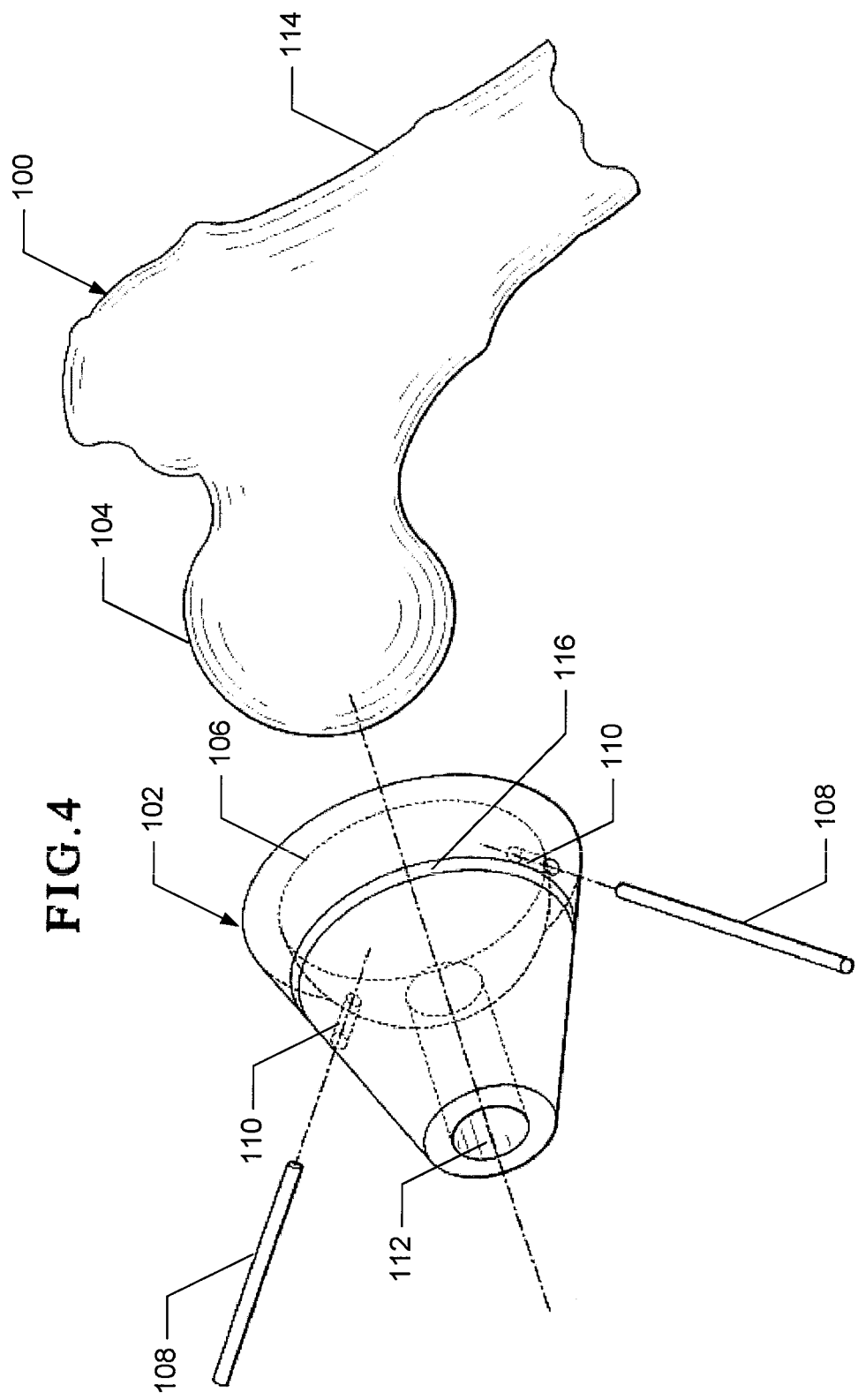
FIG. 4 is a perspective view of the femoral head positioned for insertion in to an example cone-shaped alignment mold.

The mold 102 may have any suitable shape so long as the aperture 112 can be accurately positioned over the femur head 104. As illustrated in FIG. 4, for example, the mold 102 may have a conical shape and still maintain an aperture 112 for a drill guide and for the anchor pins 108 and a guide slot 116 for an osteotomy. As can be appreciated by one of skill in the art, other shapes are also possible.

Figure 5:
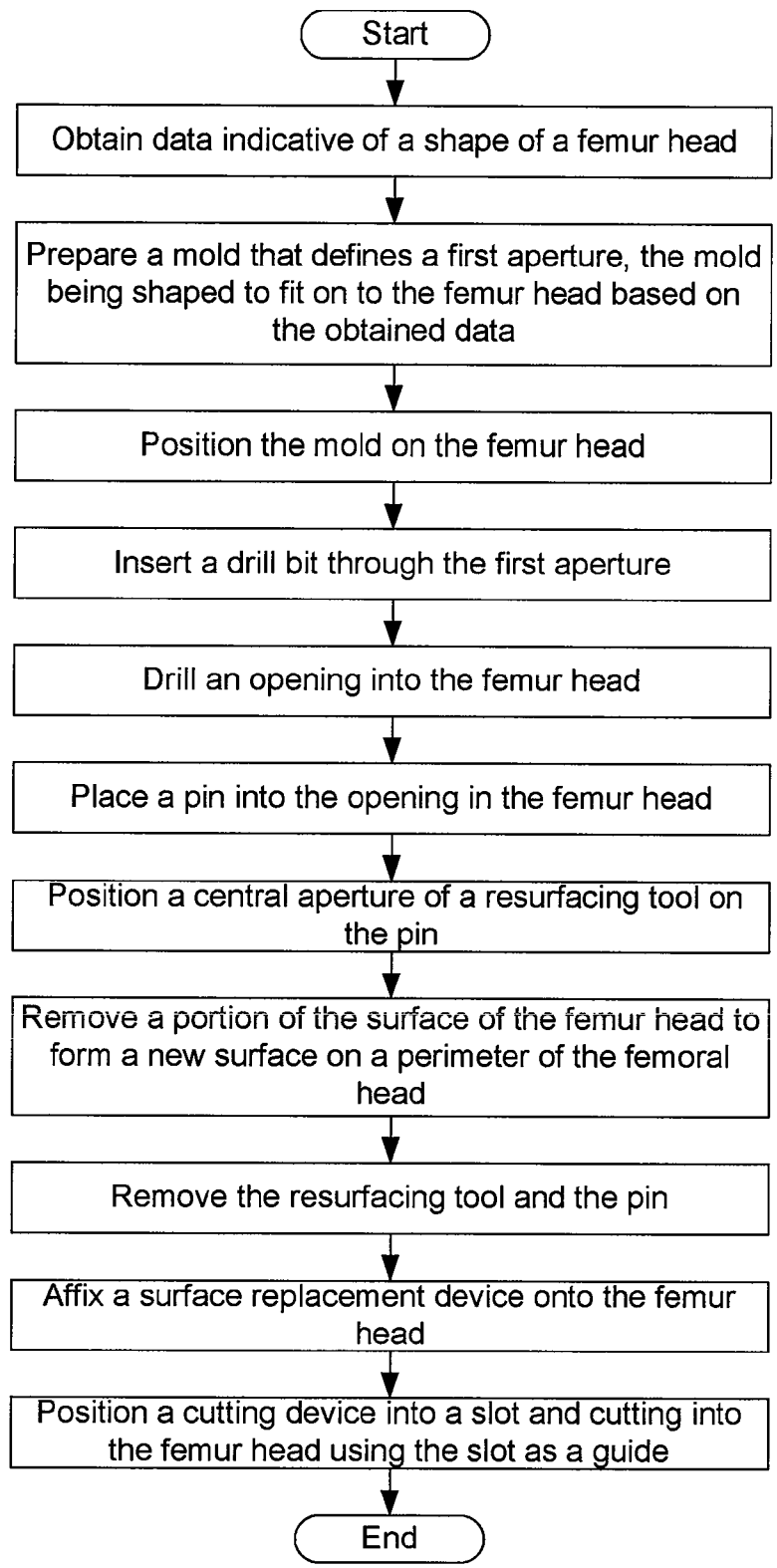
FIG. 5 is a flow chart of an example method for determining pin placement during hip surgery.

A hip surgery method is also disclosed in which an image of a patient's femur is obtained using methods such as X-rays, magnetic resonance imagery or other such techniques. The image is then used to design and prepare a mold that contains a suitably sized aperture for guiding a drill at the desired location and angle. This can most conveniently be accomplished using CAD/CAM equipment. A flow chart of an example method for determining pin placement during hip surgery is illustrated in FIG. 5.

In surgery, the embodiments are used after first exposing a patient's hip and femur head 104. The mold 102 is positioned onto the femur head 104. FIG. 3 illustrates an embodiment in which the mold 102 can only fit on to the femur head 104 in a single unique position due to the unique contoured surface 106 of the inside of the mold 102 that matches a unique contoured surface of the femur head 104. The small anchor pins 108 may be inserted through the pin placement apertures 110 in the side of the mold 102 to secure the mold 102 in place. Once the mold 102 is secured, a larger pin, drill, and/or guide wire may be inserted though the main aperture 112 of the mold 102 and into the head 104 and/or neck 114 of the patient's femur 100. Once the main pin (or other device) is in place, the mold 102 can preferably removed.

In embodiments in which the mold 102 fits the femoral head 104 in one position, the exact pin location (i.e., the entry point of the pin into the femoral head 104 and the axis of the pin relative to the femoral neck 114) is determined by the main aperture 112 of the mold 102. In addition, the size of the pin can be confirmed by the size of the main aperture 112 of the mold 102. As a result, the present technique is faster, more accurate, and less invasive than previous techniques.

The pin can be used as a guide for a cutting instrument that can be used for resurfacing the femur head 104. The central aperture of a resurfacing tool can be positioned on the pin and the tool used to remove a portion of the surface of the femoral head 104 to form a new surface on the perimeter of the femoral head 104. The femur head 104 can be reshaped into any shape that can receive a surface replacement device that creates a new femur head surface. Suitable shapes include conical shapes, tapered or conical shapes for example.

Once the femur head 104 has been reshaped, the resurfacing tool can be removed. The pin can also be removed. A replacement device bearing a new femur head surface can then be positioned on the femur head 104. The replacement device can have a portion adopted to match the reshaped surface of the femoral head 104. Further, the replacement device can have a protruding pin adapted to fit within the opening in the central axis of the femur head 104.

During the procedure the surgeon may also use the slot 116, when present, to cut the femoral head 104 (e.g., osteotomy of the femoral head 104) to prepare the femoral head 104 to receive a femoral head component. When the mold 102 only fits on to the femoral head 104 in one position, the exact location and angle of the cut can be precisely determined by the slot 116 of the mold 102. The slot 116 can be used by positioning a cutting device into the slot 116 and making a cut into the femur using the slot 116 as a guide.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of performing a portion of a hip surgery, the method comprising:
    positioning on a femur head a mold that defines a first aperture, the mold being shaped to fit on to the femur head based on data indicative of a shape of the femur head, and wherein the mold defines a slot for guiding a cutting device;
    inserting a drill bit through the first aperture; and
    drilling an opening into the femur head.

2. The method of claim 1 further comprising, placing a pin into the opening in the femur head.

3. The method of claim 2 further comprising, positioning a central aperture of a resurfacing tool on the pin and removing a portion of the surface of the femur head to form a new surface on a perimeter of the femur head.

4. The method of claim 3, wherein the new surface includes a cylindrical surface.

5. The method of claim 3 further comprising, removing the resurfacing tool and the pin and affixing a surface replacement device onto the femur head.

6. The method of claim 5, wherein the surface replacement device has a portion adapted to match the new surface of the femur head.

7. The method of claim 5, wherein the surface replacement device has a protruding pin adapted to fit within the opening in the femur head.

8. The method of claim 1, wherein the slot defines an angle, position, or depth for cutting into the femur head when the mold is positioned on the femur head.

9. The method of claim 1, further comprising placing a guide wire through the first aperture of the mold and into the femur head.

10. The method of claim 1, wherein when the mold is positioned on the femur head, the first aperture defines an axis in the femur head that is in line with a femur neck.

11. A method of performing a portion of a hip surgery, the method comprising:
    positioning on a femur head a mold that defines a first aperture, the mold being shaped to fit on to the femur head based on data indicative of a shape of the femur head, and wherein the mold defines a slot for guiding a cutting device;
    inserting a drill bit through the first aperture; and
    drilling an opening into the femur head;
    wherein the mold further defines a second aperture for a positioning pin and the positioning pin is placed through the second aperture into the femur head.

12. The method of claim 11, wherein the positioning pin secures the mold to the femur head.

13. The method of claim 11, further comprising:
    placing a pin into the opening in the femur head; and
    positioning a central aperture of a resurfacing tool on the pin and removing a portion of the surface of the femur head to form a new surface on a perimeter of the femur head.

14. The method of claim 13, further comprising removing the resurfacing tool and the pin and affixing a surface replacement device onto the femur head.

15. The method of claim 11, wherein when the mold is positioned on the femur head, the first aperture defines an axis in the femur head that is in line with a femur neck.

16. A method of performing a portion of a hip surgery, the method comprising:
   positioning on a femur head a mold that defines a first aperture, the mold being shaped to fit on to the femur head based on data indicative of a shape of the femur head, and wherein the mold defines a slot for guiding a cutting device;
   inserting a drill bit through the first aperture;
   drilling an opening into the femur head; and
   positioning a cutting device into the slot and cutting into the femur head using the slot as a guide.

17. The method of claim 16, wherein the slot defines an angle, position, or depth for cutting into the femur head when the mold is positioned on the femur head.

18. The method of claim 16, further comprising:
   placing a pin into the opening in the femur head; and
   positioning a central aperture of a resurfacing tool on the pin and removing a portion of the surface of the femur head to form a new surface on a perimeter of the femur head.

19. The method of claim 18, further comprising removing the resurfacing tool and the pin and affixing a surface replacement device onto the femur head.

20. The method of claim 16, wherein when the mold is positioned on the femur head, the first aperture defines an axis in the femur head that is in line with a femur neck.

\* \* \* \* \*